(12) United States Patent
Wilk et al.

(10) Patent No.: US 6,881,199 B2
(45) Date of Patent: Apr. 19, 2005

(54) LEFT VENTRICULAR CONDUIT WITH BLOOD VESSEL GRAFT

(75) Inventors: Peter J. Wilk, New York, NY (US);
David Y. Phelps, Louisville, KY (US);
Scott J. Wolf, Minneapolis, MN (US)

(73) Assignee: Percardia, Inc., Nashua, NH (US)

( * ) Notice: Subject to any disclaimer, the term of this patent is extended or adjusted under 35 U.S.C. 154(b) by 349 days.

(21) Appl. No.: 09/828,794

(22) Filed: Apr. 10, 2001

(65) Prior Publication Data

US 2002/0007138 A1 Jan. 17, 2002

Related U.S. Application Data

(63) Continuation of application No. 09/369,061, filed on Aug. 4, 1999, now Pat. No. 6,254,564.
(60) Provisional application No. 60/099,719, filed on Sep. 10, 1998.

(51) Int. Cl.[7] .......................... A61M 5/00; A61B 17/08; A61F 2/06; A61F 2/04
(52) U.S. Cl. .......................... 604/9; 606/153; 623/1.24; 623/23.68
(58) Field of Search .......................... 604/8–10, 27–30, 604/500, 506–9, 511, 264, 263–66, 523, 530–32, 537, 285–88; 128/898; 623/1.1, 1.11–1.12, 1.15, 1.17–1.18, 1.2, 1.21–1.25, 1.31, 1.32, 1.3, 1.36–1.39, 1.4, 1.41–1.48, 1.49, 11.11, 23.64, 23.67–23.68, 23.7–23.71, 23.75–23.76, 920, 921, 915, 916; 606/108, 151, 153, 154, 159, 167, 170, 184–185, 191–192, 194, 195, 198–200

(56) References Cited

U.S. PATENT DOCUMENTS 4,118,806 A * 10/1978 Porier et al. ............... 623/1.26
4,441,215 A 4/1984 Kaster
4,546,499 A 10/1985 Possis et al.

(Continued)

FOREIGN PATENT DOCUMENTS

| EP | 0 732 088 | 9/1996 |
|---|---|---|
| EP | 0 815 798 | 7/1997 |
| EP | 0 829 239 | 8/1997 |

(Continued)

OTHER PUBLICATIONS

US 6,331,185, 12/2001, Gambale et al. (withdrawn)
Gardner, M.D. et al., "An Experimental Anatomic Study of Indirect Myocardial Revascularization," *Journal of Surgical Research*, May 1971, vol. 11, No. 5, pp. 243–247.
Palmaz et al., "Expandable Intrahepatic Portacaval Shunt Stents: Early Experience in the Dog," *AJR*, 1985, vol. 145, pp. 821–825.
Palmaz et al., "Expandable Intrahepatic Portacaval Shunt Stents in Dogs with Chronic Portal Hypertension," *AJR*, 1986, vol. 147, pp. 1251–1254.
Richter, M.D. et al., "Transjugular Intrahepatic Portacaval Stent Shunt: Preliminary Clinical Results," *Radiology*, 1990, vol. 174, No. 3, pp. 1027–1030.

(Continued)

*Primary Examiner*—Patricia Bianco
(74) *Attorney, Agent, or Firm*—Finnegan, Henderson, Farabow, Garrett & Dunner, LLP (57) ABSTRACT

A method of flowing blood from a heart chamber to a coronary vessel includes providing a conduit with a first end and second end, providing the conduit within a heart wall such that the first end of the conduit is open towards the heart chamber and the second end is open towards the blood vessel, and during diastole, restricting a flow of blood from the coronary vessel to the heart chamber via the natural valve.

19 Claims, 2 Drawing Sheets

U.S. PATENT DOCUMENTS

| | | | |
|---|---|---|---|
| 4,562,597 A | 1/1986 | Possis et al. | |
| 4,733,665 A | 3/1988 | Palmaz | |
| 4,769,029 A | 9/1988 | Patel | |
| 4,953,553 A | 9/1990 | Tremulis | |
| 5,147,388 A | 9/1992 | Yamazaki | |
| 5,193,546 A | 3/1993 | Shaknovich | |
| 5,258,008 A | 11/1993 | Wilk | |
| 5,275,580 A | 1/1994 | Yamazaki | |
| 5,287,861 A | 2/1994 | Wilk | |
| 5,330,486 A | 7/1994 | Wilk | |
| 5,332,402 A | 7/1994 | Teitelbaum | |
| 5,344,426 A | 9/1994 | Lau et al. | |
| 5,389,096 A | 2/1995 | Aita et al. | |
| 5,409,019 A | 4/1995 | Wilk | |
| 5,411,552 A | 5/1995 | Andersen et al. | |
| 5,429,144 A * | 7/1995 | Wilk | 128/898 |
| 5,456,712 A | 10/1995 | Maginot | |
| 5,470,320 A | 11/1995 | Tifenbrun et al. | |
| 5,500,014 A | 3/1996 | Quijano et al. | |
| 5,527,337 A | 6/1996 | Stack et al. | |
| 5,545,214 A | 8/1996 | Stevens | |
| 5,554,119 A | 9/1996 | Harrison et al. | |
| 5,571,167 A | 11/1996 | Maginot | |
| 5,571,215 A | 11/1996 | Sterman et al. | |
| 5,593,434 A | 1/1997 | Williams | |
| 5,609,626 A | 3/1997 | Quijano et al. | |
| 5,618,299 A | 4/1997 | Khosravi et al. | |
| 5,655,548 A | 8/1997 | Nelson et al. | |
| 5,662,124 A | 9/1997 | Wilk | |
| 5,733,267 A | 3/1998 | Del Toro | |
| 5,755,682 A | 5/1998 | Knudson | |
| 5,758,663 A | 6/1998 | Wilk et al. | |
| 5,797,946 A | 8/1998 | Chin | |
| 5,807,384 A | 9/1998 | Mueller | |
| 5,810,836 A | 9/1998 | Hussein et al. | |
| 5,824,038 A | 10/1998 | Wall | |
| 5,824,071 A | 10/1998 | Nelson et al. | |
| 5,830,222 A | 11/1998 | Makower | |
| 5,840,081 A | 11/1998 | Andersen et al. | |
| 5,865,723 A | 2/1999 | Love | |
| 5,876,373 A | 3/1999 | Giba et al. | |
| 5,878,751 A | 3/1999 | Hussein et al. | |
| 5,885,259 A | 3/1999 | Berg | |
| 5,908,028 A | 6/1999 | Wilk | |
| 5,908,029 A | 6/1999 | Knudson et al. | |
| 5,922,022 A | 7/1999 | Nash et al. | |
| 5,925,012 A | 7/1999 | Murphy-Chutorian et al. | |
| 5,931,848 A | 8/1999 | Saadat | |
| 5,935,119 A | 8/1999 | Guy et al. | |
| 5,935,161 A | 8/1999 | Robinson et al. | |
| 5,938,632 A | 8/1999 | Ellis | |
| 5,944,019 A * | 8/1999 | Knudson et al. | 128/898 |
| 5,971,993 A | 10/1999 | Hussein et al. | |
| 5,976,155 A | 11/1999 | Foreman et al. | |
| 5,976,178 A | 11/1999 | Goldstein et al. | |
| 5,976,192 A | 11/1999 | McIntyre et al. | |
| 5,976,650 A | 11/1999 | Campbell et al. | |
| 5,979,455 A | 11/1999 | Maginot | |
| 5,980,533 A | 11/1999 | Holman | |
| 5,980,548 A | 11/1999 | Evans et al. | |
| 5,984,956 A | 11/1999 | Tweden et al. | |
| 5,989,276 A | 11/1999 | Houser et al. | |
| 5,989,287 A | 11/1999 | Yang et al. | |
| 5,993,481 A | 11/1999 | Marcade et al. | |
| 5,997,525 A | 12/1999 | March et al. | |
| 5,997,563 A | 12/1999 | Kretzers | |
| 5,997,573 A | 12/1999 | Quijano et al. | |
| 5,999,678 A | 12/1999 | Murphy-Chutorian et al. | |
| 6,001,123 A | 12/1999 | Lau | |
| 6,004,261 A | 12/1999 | Sinofsky et al. | |
| 6,004,347 A | 12/1999 | McNamara et al. | |
| 6,004,348 A | 12/1999 | Banas et al. | |
| 6,007,543 A | 12/1999 | Ellis et al. | |
| 6,010,449 A | 1/2000 | Selmon et al. | |
| 6,026,814 A | 2/2000 | LaFontaine et al. | |
| 6,029,672 A | 2/2000 | Vanney et al. | |
| 6,033,582 A | 3/2000 | Lee et al. | |
| 6,035,856 A | 3/2000 | LaFontaine et al. | |
| 6,036,677 A | 3/2000 | Javier, Jr. et al. | |
| 6,036,697 A | 3/2000 | DiCaprio | |
| 6,042,581 A | 3/2000 | Ryan et al. | |
| 6,045,565 A | 4/2000 | Ellis et al. | |
| 6,053,924 A | 4/2000 | Hussein | |
| 6,053,942 A | 4/2000 | Eno et al. | |
| 6,056,743 A | 5/2000 | Ellis et al. | |
| 6,067,988 A | 5/2000 | Mueller | |
| 6,068,638 A | 5/2000 | Makower | |
| 6,071,292 A | 6/2000 | Makower et al. | |
| 6,076,529 A | 6/2000 | Vanney et al. | |
| 6,080,163 A | 6/2000 | Hussein et al. | |
| 6,080,170 A | 6/2000 | Nash et al. | |
| 6,092,526 A | 7/2000 | LaFontaine et al. | |
| 6,093,166 A | 7/2000 | Knudson et al. | |
| 6,093,177 A | 7/2000 | Javier, Jr. et al. | |
| 6,093,185 A | 7/2000 | Ellis et al. | |
| 6,102,941 A | 8/2000 | Tweden et al. | |
| 6,113,630 A | 9/2000 | Vanney et al. | |
| 6,113,823 A | 9/2000 | Eno | |
| 6,120,520 A | 9/2000 | Saadat et al. | |
| 6,123,682 A | 9/2000 | Knudson et al. | |
| 6,126,649 A | 10/2000 | VanTassel et al. | |
| 6,126,654 A | 10/2000 | Giba et al. | |
| 6,126,686 A * | 10/2000 | Badylak et al. | 623/1.24 |
| 6,132,451 A | 10/2000 | Payne et al. | |
| 6,139,541 A | 10/2000 | Vanney et al. | |
| 6,155,264 A | 12/2000 | Ressemann et al. | |
| 6,156,031 A | 12/2000 | Aita et al. | |
| 6,157,852 A | 12/2000 | Selmon et al. | |
| 6,159,225 A | 12/2000 | Makower | |
| 6,162,245 A | 12/2000 | Jayaraman | |
| 6,165,185 A | 12/2000 | Shennib et al. | |
| 6,165,188 A | 12/2000 | Saadat et al. | |
| 6,168,614 B1 | 1/2001 | Andersen et al. | |
| 6,171,251 B1 | 1/2001 | Mueller et al. | |
| 6,182,668 B1 | 2/2001 | Tweden et al. | |
| 6,186,972 B1 | 2/2001 | Nelson et al. | |
| 6,190,353 B1 | 2/2001 | Makower et al. | |
| 6,193,726 B1 | 2/2001 | Vanney | |
| 6,196,230 B1 | 3/2001 | Hall et al. | |
| 6,197,050 B1 | 3/2001 | Eno et al. | |
| 6,197,296 B1 * | 3/2001 | Davies et al. | 424/93.7 |
| 6,197,324 B1 | 3/2001 | Crittenden | |
| 6,200,311 B1 | 3/2001 | Danek et al. | |
| 6,203,556 B1 | 3/2001 | Evans et al. | |
| 6,213,126 B1 | 4/2001 | LaFontaine et al. | |
| 6,214,041 B1 | 4/2001 | Tweden et al. | |
| 6,217,527 B1 | 4/2001 | Selmon et al. | |
| 6,217,549 B1 | 4/2001 | Selmon et al. | |
| 6,217,575 B1 | 4/2001 | DeVore et al. | |
| 6,221,049 B1 | 4/2001 | Selmon et al. | |
| 6,223,752 B1 | 5/2001 | Vanney et al. | |
| 6,224,584 B1 | 5/2001 | March et al. | |
| 6,231,546 B1 | 5/2001 | Milo et al. | |
| 6,231,551 B1 | 5/2001 | Barbut | |
| 6,231,587 B1 | 5/2001 | Makower | |
| 6,235,000 B1 | 5/2001 | Milo et al. | |
| 6,237,607 B1 | 5/2001 | Vanney et al. | |
| 6,238,406 B1 | 5/2001 | Ellis et al. | |
| 6,241,667 B1 | 6/2001 | Vetter et al. | |
| 6,241,741 B1 * | 6/2001 | Duhaylongsod et al. | 606/153 |
| 6,248,112 B1 | 6/2001 | Gambale et al. | |

| | | | | | | |
|---|---|---|---|---|---|---|
| 6,250,305 B1 | 6/2001 | Tweden | | 6,685,648 B1 | 2/2004 | Flaherty et al. |
| 6,251,079 B1 | 6/2001 | Gambale et al. | | 6,694,983 B1 | 2/2004 | Wolf et al. |
| 6,251,116 B1 | 6/2001 | Shennib et al. | | 2001/0000041 A1 | 3/2001 | Selmon et al. |
| 6,251,418 B1 | 6/2001 | Ahern et al. | | 2001/0004683 A1 | 6/2001 | Gambale et al. |
| 6,253,768 B1 | 7/2001 | Wilk | | 2001/0004690 A1 | 6/2001 | Gambale et al. |
| 6,253,769 B1 | 7/2001 | LaFontaine et al. | | 2001/0004699 A1 | 6/2001 | Gittings et al. |
| 6,254,564 B1 * | 7/2001 | Wilk et al. ................... 604/9 | | 2001/0008969 A1 | 7/2001 | Evans et al. |
| 6,258,052 B1 | 7/2001 | Milo | | 2001/0012948 A1 | 8/2001 | Vanney |
| 6,258,119 B1 | 7/2001 | Hussein et al. | | 2001/0014813 A1 | 8/2001 | Saadat et al. |
| 6,261,304 B1 | 7/2001 | Hall et al. | | 2001/0016700 A1 | 8/2001 | Eno et al. |
| 6,283,951 B1 | 9/2001 | Flaherty et al. | | 2001/0018596 A1 | 8/2001 | Selmon et al. |
| 6,283,983 B1 | 9/2001 | Makower et al. | | 2001/0020172 A1 | 9/2001 | Selmon et al. |
| 6,285,903 B1 | 9/2001 | Rosenthal et al. | | 2001/0025643 A1 | 10/2001 | Foley |
| 6,287,317 B1 | 9/2001 | Makower et al. | | 2001/0027287 A1 | 10/2001 | Shmulewitz et al. |
| 6,290,709 B1 | 9/2001 | Ellis et al. | | 2001/0029385 A1 | 10/2001 | Shennib et al. |
| 6,290,728 B1 | 9/2001 | Phelps et al. | | 2001/0034547 A1 | 10/2001 | Hall et al. |
| 6,302,875 B1 | 10/2001 | Makower et al. | | 2001/0037117 A1 | 11/2001 | Gambale et al. |
| 6,322,548 B1 | 11/2001 | Payne et al. | | 2001/0037149 A1 | 11/2001 | Wilk |
| 6,330,884 B1 | 12/2001 | Kim | | 2001/0039426 A1 | 11/2001 | Makower et al. |
| 6,350,248 B1 | 2/2002 | Knudson et al. | | 2001/0039445 A1 | 11/2001 | Hall et al. |
| 6,361,519 B1 | 3/2002 | Knudson et al. | | 2001/0041902 A1 | 11/2001 | Lepulu et al. |
| 6,363,938 B1 | 4/2002 | Saadat et al. | | 2001/0044631 A1 | 11/2001 | Akin et al. |
| 6,363,939 B1 | 4/2002 | Wilk | | 2001/0047165 A1 | 11/2001 | Makower et al. |
| 6,375,615 B1 | 4/2002 | Flaherty et al. | | 2001/0049523 A1 | 12/2001 | DeVore et al. |
| 6,379,319 B1 | 4/2002 | Garibotto et al. | | 2001/0053932 A1 | 12/2001 | Phelps et al. |
| 6,387,119 B1 | 5/2002 | Wolf et al. | | 2002/0002349 A1 | 1/2002 | Flaherty et al. |
| 6,390,098 B1 | 5/2002 | LaFontaine et al. | | 2002/0004662 A1 | 1/2002 | Wilk |
| 6,395,208 B1 | 5/2002 | Herweck et al. | | 2002/0004663 A1 | 1/2002 | Gittings et al. |
| 6,402,740 B1 | 6/2002 | Ellis et al. | | 2002/0007138 A1 | 1/2002 | Wilk et al. |
| 6,406,488 B1 | 6/2002 | Tweden et al. | | 2002/0029079 A1 | 3/2002 | Kim et al. |
| 6,406,491 B1 | 6/2002 | Vanney | | 2002/0032476 A1 | 3/2002 | Gambale et al. |
| 6,409,697 B1 | 6/2002 | Eno et al. | | 2002/0049486 A1 | 4/2002 | Knudson et al. |
| 6,409,751 B1 | 6/2002 | Hall et al. | | 2002/0058897 A1 | 4/2002 | Renati |
| 6,416,490 B1 | 7/2002 | Ellis et al. | | 2002/0062146 A1 | 5/2002 | Makower et al. |
| 6,423,089 B1 | 7/2002 | Gingras et al. | | 2002/0065478 A1 | 5/2002 | Knudson et al. |
| 6,432,119 B1 | 8/2002 | Saadat | | 2002/0072699 A1 | 6/2002 | Knudson et al. |
| 6,432,126 B1 | 8/2002 | Gambale et al. | | 2002/0077566 A1 | 6/2002 | Laroya et al. |
| 6,432,127 B1 | 8/2002 | Kim et al. | | 2002/0077654 A1 | 6/2002 | Javier, Jr. et al. |
| 6,432,132 B1 | 8/2002 | Cottone et al. | | 2002/0092535 A1 | 7/2002 | Wilk |
| 6,443,158 B1 | 9/2002 | LaFontaine et al. | | 2002/0092536 A1 | 7/2002 | LaFontaine et al. |
| 6,447,522 B1 | 9/2002 | Gambale et al. | | 2002/0095111 A1 | 7/2002 | Tweden et al. |
| 6,447,539 B1 | 9/2002 | Nelson et al. | | 2002/0100484 A1 | 8/2002 | Hall et al. |
| 6,454,760 B1 | 9/2002 | Vanney | | 2002/0111627 A1 | 8/2002 | Kim et al. |
| 6,454,794 B1 | 9/2002 | Knudson et al. | | 2002/0123698 A1 | 9/2002 | Garibotto et al. |
| 6,458,092 B1 | 10/2002 | Gambale et al. | | 2002/0123786 A1 * | 9/2002 | Gittings et al. ............ 623/1.11 |
| 6,458,140 B1 | 10/2002 | Akin et al. | | 2002/0138087 A1 | 9/2002 | Shennib et al. |
| 6,458,323 B1 | 10/2002 | Boekstegers | | 2002/0143285 A1 | 10/2002 | Eno et al. |
| 6,464,709 B1 | 10/2002 | Shennib et al. | | 2002/0143289 A1 | 10/2002 | Ellis et al. |
| 6,475,226 B1 | 11/2002 | Belef et al. | | 2002/0144696 A1 | 10/2002 | Sharkaway et al. |
| 6,475,244 B1 | 11/2002 | Herweck et al. | | 2002/0161383 A1 | 10/2002 | Akin et al. |
| 6,482,220 B1 | 11/2002 | Mueller | | 2002/0161424 A1 | 10/2002 | Rapacki et al. |
| 6,491,689 B1 | 12/2002 | Ellis et al. | | 2002/0165479 A1 | 11/2002 | Wilk |
| 6,491,707 B1 | 12/2002 | Makower et al. | | 2002/0165606 A1 | 11/2002 | Wolf et al. |
| 6,508,825 B1 | 1/2003 | Selmon et al. | | 2002/0179098 A1 | 12/2002 | Makower et al. |
| 6,511,458 B1 | 1/2003 | Milo et al. | | 2002/0183716 A1 | 12/2002 | Herweck et al. |
| 6,514,217 B1 | 2/2003 | Selmon et al. | | 2002/0193782 A1 | 12/2002 | Ellis et al. |
| 6,514,271 B1 | 2/2003 | Evans et al. | | 2003/0018379 A1 | 1/2003 | Knudson et al. |
| 6,517,558 B1 | 2/2003 | Gittings et al. | | 2003/0044315 A1 | 3/2003 | Boekstegers |
| 6,524,323 B1 | 2/2003 | Nash et al. | | 2003/0045828 A1 | 3/2003 | Wilk |
| 6,544,230 B1 | 4/2003 | Flaherty et al. | | 2003/0055371 A1 | 3/2003 | Wolf et al. |
| 6,559,132 B1 | 5/2003 | Holmer | | 2003/0073973 A1 | 4/2003 | Evans et al. |
| 6,561,998 B1 | 5/2003 | Roth et al. | | 2003/0078561 A1 | 4/2003 | Gambale et al. |
| 6,565,528 B1 | 5/2003 | Mueller | | 2003/0100920 A1 | 5/2003 | Akin et al. |
| 6,565,594 B1 | 5/2003 | Herweck et al. | | 2003/0105514 A1 | 6/2003 | Phelps et al. |
| 6,569,145 B1 | 5/2003 | Shmulewitz et al. | | 2003/0120195 A1 | 6/2003 | Milo et al. |
| 6,569,147 B1 | 5/2003 | Evans et al. | | 2003/0181938 A1 | 9/2003 | Roth et al. |
| 6,610,100 B1 | 8/2003 | Phelps et al. | | 2003/0195458 A1 | 10/2003 | Phelps et al. |
| 6,641,610 B1 | 11/2003 | Wolf et al. | | 2003/0216679 A1 | 11/2003 | Wolf et al. |
| 6,651,670 B1 | 11/2003 | Rapacki et al. | | 2003/0236542 A1 | 12/2003 | Makower |
| 6,666,863 B1 | 12/2003 | Wentzel et al. | | 2004/0015225 A1 | 1/2004 | Kim et al. |
| 6,669,709 B1 | 12/2003 | Cohn et al. | | 2004/0019348 A1 | 1/2004 | Stevens et al. |

FOREIGN PATENT DOCUMENTS

| | | |
|---|---|---|
| EP | 0 792 624 | 9/1997 |
| EP | 0 797 957 | 10/1997 |
| EP | 0 797 958 | 10/1997 |
| EP | 0 799 604 | 10/1997 |
| EP | 0 801 928 | 10/1997 |
| EP | 0 836 834 | 10/1997 |
| EP | 0 876 796 | 5/1998 |
| EP | 0 853 921 | 7/1998 |
| EP | 0 858 779 | 8/1998 |
| EP | 0 876 803 | 11/1998 |
| EP | 0 888 750 | 1/1999 |
| EP | 0 895 752 | 2/1999 |
| EP | 1 020 166 | 7/2000 |
| EP | 1 027 870 | 8/2000 |
| EP | 1 097 676 | 5/2001 |
| EP | 1 166 721 | 1/2002 |
| EP | 0 959 815 | 12/2002 |
| GB | 2 316 322 | 2/1998 |
| WO | WO 96/32972 | 10/1996 |
| WO | WO 96/35469 | 11/1996 |
| WO | WO 96/39962 | 12/1996 |
| WO | WO 96/39964 | 12/1996 |
| WO | WO 96/39965 | 12/1996 |
| WO | 97/13463 | 4/1997 |
| WO | 97/13471 | 4/1997 |
| WO | 97/27893 | 8/1997 |
| WO | 97/27897 | 8/1997 |
| WO | WO 97/27898 | 8/1997 |
| WO | 97/32551 | 9/1997 |
| WO | WO 97/43961 | 11/1997 |
| WO | WO 98/03118 | 1/1998 |
| WO | 98/06356 | 2/1998 |
| WO | 98/08456 | 3/1998 |
| WO | 98/10714 | 3/1998 |
| WO | 98/16161 | 4/1998 |
| WO | WO 98/24373 | 6/1998 |
| WO | WO 98/25533 | 6/1998 |
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | 98/44869 | 10/1998 |
| WO | 98/46115 | 10/1998 |
| WO | 98/46119 | 10/1998 |
| WO | 98/49964 | 11/1998 |
| WO | 98/53759 | 12/1998 |
| WO | 98/55027 | 12/1998 |
| WO | WO 98/57590 | 12/1998 |
| WO | 98/57591 | 12/1998 |
| WO | WO 98/57592 | 12/1998 |
| WO | WO 99/07296 | 2/1999 |
| WO | 99/08624 | 2/1999 |
| WO | 99/49793 | 3/1999 |
| WO | WO 99/15220 | 4/1999 |
| WO | WO 99/17671 | 4/1999 |
| WO | 99/17683 | 4/1999 |
| WO | 99/21490 | 5/1999 |
| WO | 99/21510 | 5/1999 |
| WO | WO 99/22655 | 5/1999 |
| WO | 99/22656 | 5/1999 |
| WO | WO 99/22658 | 5/1999 |
| WO | 99/25273 | 5/1999 |
| WO | WO 99/27985 | 6/1999 |
| WO | WO 99/35977 | 7/1999 |
| WO | WO 99/35979 | 7/1999 |
| WO | WO 99/35980 | 7/1999 |
| WO | 99/36000 | 7/1999 |
| WO | 99/36001 | 7/1999 |
| WO | 99/38459 | 8/1999 |
| WO | WO 99/40853 | 8/1999 |
| WO | 99/40868 | 8/1999 |
| WO | WO 99/40963 | 8/1999 |
| WO | WO 99/44524 | 9/1999 |
| WO | 99/47071 | 9/1999 |
| WO | 99/48545 | 9/1999 |
| WO | WO 99/48549 | 9/1999 |
| WO | 99/49910 | 10/1999 |
| WO | 99/51162 | 10/1999 |
| WO | 99/53863 | 10/1999 |
| WO | WO 99/55406 | 11/1999 |
| WO | 99/60941 | 12/1999 |
| WO | 99/62430 | 12/1999 |
| WO | 00/09195 | 2/2000 |
| WO | WO 00/15275 | 2/2000 |
| WO | 00/10623 | 3/2000 |
| WO | 00/12029 | 3/2000 |
| WO | WO 00/13722 | 3/2000 |
| WO | 00/15146 | 3/2000 |
| WO | 00/15147 | 3/2000 |
| WO | WO 00/15148 | 3/2000 |
| WO | 00/15148 | 3/2000 |
| WO | 00/15149 | 3/2000 |
| WO | 00/15275 | 3/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/28924 | 5/2000 |
| WO | 00/33725 | 6/2000 |
| WO | WO 00/35376 | 6/2000 |
| WO | WO 00/36997 | 6/2000 |
| WO | 00/41632 | 7/2000 |
| WO | 00/41633 | 7/2000 |
| WO | WO 00/43051 | 7/2000 |
| WO | 00/45711 | 8/2000 |
| WO | WO 00/45886 | 8/2000 |
| WO | 00/47139 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | 00/56387 | 9/2000 |
| WO | 00/60995 | 10/2000 |
| WO | 00/66007 | 11/2000 |
| WO | 00/66009 | 11/2000 |
| WO | 00/66035 | 11/2000 |
| WO | WO 00/69345 | 11/2000 |
| WO | WO 00/69504 | 11/2000 |
| WO | 00/71195 | 11/2000 |
| WO | WO 01/08566 | 2/2001 |
| WO | WO 01/08602 | 2/2001 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | 01/17440 | 3/2001 |
| WO | 1 097 676 | 5/2001 |
| WO | 01/49187 | 7/2001 |

OTHER PUBLICATIONS

Zemel, M.D. et al., "Percutaneous Transjugular Portosystemic Shunt," *JAMA,* 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons,* Aug. 1997, vol. 34, No. 2, pp. 257–264.

Lary, M.D. et al., "Myocardial Revascularization Experiments Using the Epicardium," *Archives of Surgery,* Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery,* Jul. 1969, vol. 58, No. 1, pp. 25–32.

Kuzela, M.D. et al., "Experimental evaluation fo direct transventricular revascularization," *The Journal of Thoracic and Cardiovascular Surgery,* Jun. 1969, vol. 57, No. 6, pp. 770–773.

Levinsky, L. et al., "The Revival of the Horseshoe Graft," *Thorac.cardiovasc. Surgeon,* 27, pp. 322–324, 1979.

Mills, Noel L. et al., "Valvulotomy of valves in the saphenous vein graft before coronary artery bypass," *The Journal of Thoracic and Cardiovascular Surgery,* 71(6), pp. 878–879, Jun. 1976.

Baba et al., "Hemodynamic effects of venous valves in aorto–coronary bypass grafts," *The Journal of Thoracic and Cardiovascular Surgery,* 71(5), pp. 774–778, May 1976.

Phillips, Steven J. M.D. et al, "Improvement in Forward Coronary Blood Flow by Using a Reversed Saphenous Vein with a Competent Valve," *The Annals of Thoracic Surgery,* 21(1), pp. 12–15, Jan. 1976.

Tweden et al., "Ventriculocoronary Artery Bypass (VCAB), a Novel Approach to Myocardial Revascularization," #2000–4653, Feb. 2000.

Publication No. US 2001/0004699 A1, published Jun. 21, 2001.

*American Medical Association Publication*; International Cardiovascular Society, "Myocardial Boring for the Ischemic Heart," A. Wakabayashi, M.D., et al.; Fifteenth Scientific Meeting, Atlantic City, NJ, Jun. 16 and 17, 1967; *Archives of Surgery*; pp. 743–752, vol. 95, No. 5, Nov. 1967.

*The Journal of Thoracic and Cardiovascular Surgery*, "Experimental Evaluation of Myocardial Tunnelization as a Method of Myocardial Revascularization," I. Anabtawi, M.D., et al., pp. 638–646., Nov. 1969.

*American Heart Journal*, "Effects of Laser Irradiation Delivered by Flexible Fiberoptic System on the Left Ventricular Internal Myocardium," G. Lee, M.D., et al., pp. 587–590, vol. 106, No. 3, Sep. 1983.

* cited by examiner

LEFT VENTRICULAR CONDUIT WITH BLOOD VESSEL GRAFT

CROSS-REFERENCE TO RELATED APPLICATION

This is a continuation of U.S. application Ser. No. 09/369,061, filed Aug. 4, 1999 now U.S. Pat. No. 6,254,564, which claims the benefits of U.S. Provisional Application No. 60/099,719, filed Sep. 10, 1998, all of which are incorporated herein by reference.

FIELD OF THE INVENTION

This invention relates to apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations having a blood vessel graft incorporated therein for controlling the flow of blood through the conduit to achieve bypass of an occluded or stenosed coronary artery.

BACKGROUND OF THE INVENTION

Coronary artery disease is a major problem in the U.S. and throughout the world. Coronary arteries as well as other blood vessels frequently become clogged with plaque which, at the very least, can reduce blood and oxygen flow to the heart muscle (myocardium), and may impair the efficiency of the heart's pumping action, and can lead to heart attack (myocardial infarction) and death. In some cases, these coronary arteries can be unblocked through noninvasive techniques such as balloon angioplasty. In more difficult cases, a surgical bypass of the blocked vessel is necessary.

In a coronary bypass operation, one or more venous segments are inserted between the aorta and the coronary artery, or, alternatively, the distal end of an internal mammary artery is anastomosed to the coronary artery at a site distal to the stenosis or occlusion. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass graft (CABG) surgery, however, is a very intrusive procedure which is expensive, time-consuming, and traumatic to the patient. The operation requires an incision through the patient's sternum (sternotomy), and that the patient be placed on a heart-lung bypass pump so that the heart can be operated on while not beating. A saphenous vein graft is harvested from the patient's leg, another highly invasive procedure, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type or location of the blockage or stenosis, or due to the risk of emboli.

Thus, there is a need for an improved coronary bypass system which is less traumatic to the patient.

SUMMARY OF THE INVENTION

The present invention addresses the need in the previous technology by providing a coronary bypass system which avoids a sternotomy and other intrusive aspects associated with coronary bypass surgery. It also frees the surgeon from having to perform multiple anastomoses, as is necessary in the current process.

The present device provides a conduit for diverting blood directly from a heart chamber, such as the left ventricle of the heart, to the coronary artery distal to the blockage or stenosis, thereby bypassing the blocked portion of the vessel. The conduit comprises a tube adapted to be positioned in the heart wall and having a section of blood vessel attached to the interior of the conduit, to provide a passage for blood flow which is similar to the body's own blood vessels.

The conduit device is delivered through the coronary artery to a position distal the blockage or stenosis. At that position, the coronary artery and the wall of the left ventricle, including the myocardium, are pierced to provide an opening or channel completely through from the coronary artery to the left ventricle of the heart. The conduit is then positioned in the opening to provide a permanent passage for blood to flow between the left ventricle of the heart and the coronary artery, distal to the blockage or stenosis.

The conduit is sized so that one open end is positioned within the coronary artery, while the other open end is positioned in the left ventricle. Prior to implantation of the conduit, a section of vein or other blood vessel is obtained from the patient, from another human donor, or from a nonhuman animal. The vein or other blood vessel is sized so as to fit within the interior of the conduit. The hollow lumen of the conduit with the blood vessel graft inserted therein provides a passage for the flow of blood.

If desired, the section of blood vessel inserted into the conduit may include one or more naturally occurring one-way valves. The valve prevents the backflow of blood from the myocardium into the left ventricle. For example, a section of vein having a valve therein can be used. Alternatively, the pulmonic valve or aortic valve obtained from a nonhuman animal, such as a fetal pig or piglet, can be used to provide a one-way passage for the flow of blood through the conduit.

DETAILED DESCRIPTION OF THE PREFERRED EMBODIMENT

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the rest of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

As used herein, the term "heart chamber" primarily refers to the interior, or lumenal, aspect of the left or right ventricle or the left or right atrium. The term "conduit," "stent," and "tube" herein refer to physical structures, preferably primarily artificial, that can be positioned between two or more chambers or vessels, to allow blood flow from one chamber or vessel to another. A "shunt" is any natural or artificial passage between natural channels, such as heart chambers or blood vessels. The conduit in the preferred arrangement can be made of a variety of materials, including various metals, such as nitinol, or plastics.

As used herein, the term "heart wall" comprises any one or more of the following portions or layers of the mammalian heart: the epicardium, myocardium, endocardium, pericardium, interatrial septum, and interventricular septum.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other nonmyocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the obstructions that are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In order to restore the flow of oxygenated blood through the coronary artery, the preferred arrangement provides for the shunting of blood directly from the heart to a site in the coronary artery which is distal the blockage or stenosis.

Although the specification herein will describe the conduit primarily with reference to the left ventricle, the preferred arrangement can be used with any of the four heart chambers, and with any coronary artery, including the left main coronary artery, the right coronary artery, the left anterior descending artery, the left circumflex artery, the posterior descending artery, the obtuse marginal branch or a diagonal branch.

A tunnel or opening is formed through the wall of the coronary artery and the myocardium and into the left ventricle of the heart which lies beneath, or deep to, the coronary artery. A conduit is positioned in the opening to keep it open.

The conduit may be introduced into the myocardium in a variety of ways, including by a catheter threaded through the femoral artery into the aorta and thence into the left ventricle and, if necessary, the left atrium; or by a catheter threaded through the femoral vein into the inferior vena cava and thence into the right atrium and right ventricle. Alternatively, the conduit may be introduced through a surgical incision in chest wall (thoracotomy) or sternum (sternotomy).

Further details regarding conduits and conduit delivery systems are described in copending patent applications entitled, DESIGNS FOR LEFT VENTRICULAR CONDUIT, U.S. application Ser. No. 09/369,048, filed Aug. 4, 1999, VALVE DESIGNS FOR LEFT VENTRICULAR CONDUIT, U.S. application Ser. No. 09/368,393, filed Aug. 4, 1999, LEFT VENTRICULAR CONDUITS TO CORONARY ARTERIES AND METHODS FOR CORONARY BYPASS, U.S. Application Ser. No. 09/534,038, filed Mar. 24, 2000, and BLOOD FLOW CONDUIT DELIVERY SYSTEM AND METHOD OF USE, U.S. application Ser. No. 09/368,644, filed Aug. 4, 1999, and U.S. Pat. Nos. 6,261,304, 5,429,144 and 5,662,124, the disclosures of which are all hereby incorporated by reference in their entirety.

The opening through the heart wall (including endocardium, myocardium, and epicardium) and coronary artery can be formed in a variety of ways, including by knife or scalpel, electrocautery, cryoablation, radiofrequency ablation, ultrasonic ablation, and the like. Other methods will be apparent to those of ordinary skill in the art.

The conduit is provided with a section of vein or other blood vessel positioned within its interior lumen. The section of vein or other blood vessel is obtained from the patient, from a donor, or from an animal. Prior to implantation of the conduit, a segment of blood vessel sized to fit with the lumen of the conduit is inserted into the conduit. The conduit with the graft therein provides a passage for the flow of blood which is similar to the natural human blood vessels. The segment of vein or other blood vessel harvested to fit within the conduit may include one or more of the valves which naturally occur in the human body. These valves act to prevent the backflow of blood. In the conduit, these naturally occurring venous valves prevent the blood from flowing back into the left ventricle of the heart from the coronary artery. The segment of vein is preferably inserted into the conduit prior to the conduit's deployment into the human body by any of various surgical or catheter-guided techniques known to those of skill in the art.

Figure 1A:
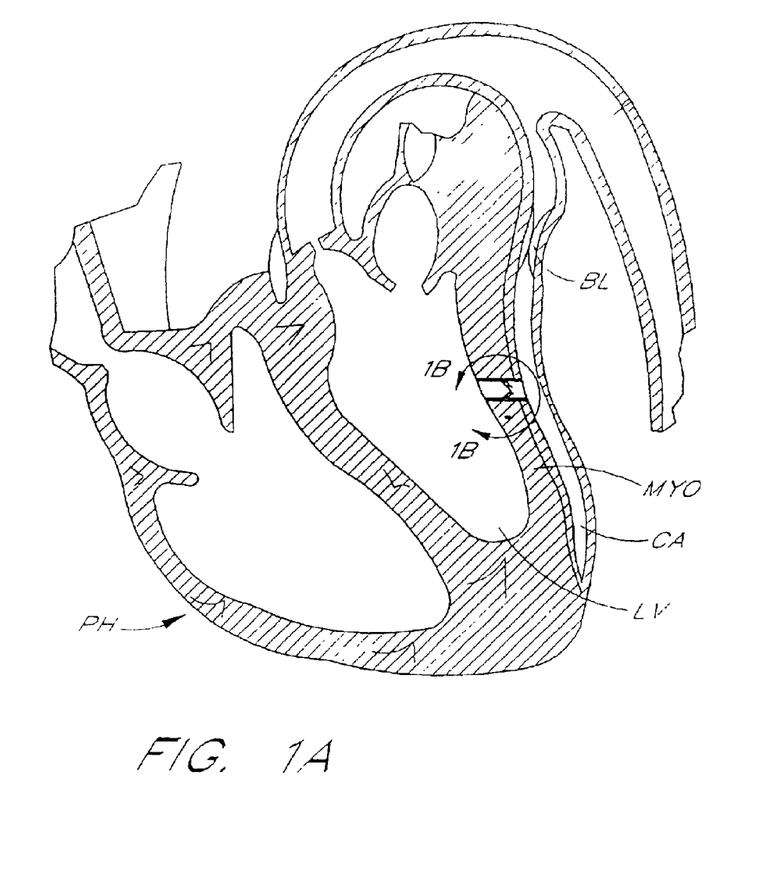
FIG. 1A is a schematic, cross-sectional view of a human heart, showing a conduit in the myocardium of the heart for forming a bypass between the left ventricle and a coronary artery.
Figure 1B:
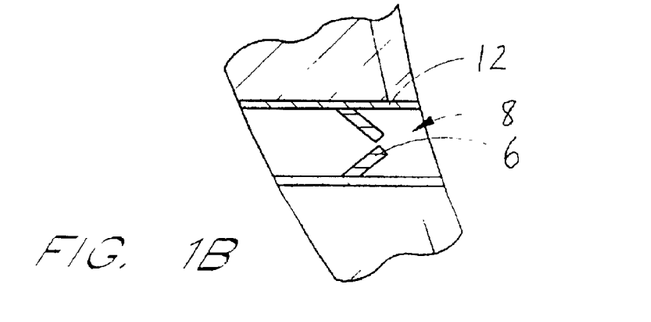
FIG. 1B is an enlarged view of the bypass conduit of FIG. 1A.

Referring now to FIGS. 1A and 1B, a coronary artery bypass is accomplished by disposing a conduit 12 (FIG. 1B) in a heart wall or myocardium MYO of a patient's heart PH (FIG. 1A). The conduit 12 preferably extends from the left ventricle LV of heart PH to a clogged coronary artery CA at a point downstream of a blockage BL to create a passageway 8 therethrough. Conduit 12 is preferably made of a biocompatible material such as stainless steel or nitinol, although other materials such as Ti, Ti alloys, Ni alloys, Co alloys and biocompatible polymers may also be used. In one embodiment, conduit 12 has a one way valve 6 to allow blood to flow from the left ventricle LV to the coronary artery CA. Although the conduit 12 may elastically deform under the contractive pressure of the heart muscle during systole, the stent remains open to allow blood to pass from the patient's left ventricle LV into the coronary artery CA. During diastole, the blood pumped into coronary artery through passageway 8 is blocked by one-way valve 6 from returning to left ventricle LV.

Figure 2:
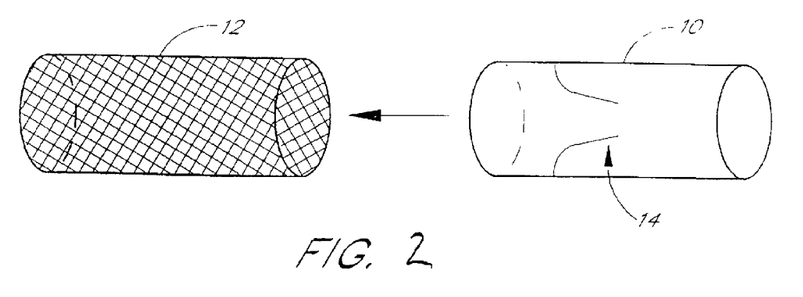
FIG. 2 is an exploded view of a vein graft incorporated into a heart conduit in accordance with the preferred arrangement.

As shown in FIG. 2, a preferred embodiment involves the use of a vein graft 10 taken from the patient. Prior to preparing the conduit 12 for placement in the patient, a section of vein 10 is obtained from the patient (i.e., an autologous graft or autograft). Of course, a blood vessel taken from another human donor (i.e., an allogeneic graft or allograft) or nonhuman animal species (i.e., a heterologous graft or xenograft) could also be used. The vein 10 is preferably taken from the saphenous vein in the leg of the patient. Alternatively, a donor vein could be used, or a fetal pig or piglet can be obtained and dissected to remove a section of the pulmonary artery having a pulmonic valve therein, or a section of the aorta having an aortic valve therein, or a similar vessel having a naturally occurring valve system. In other embodiments, the endothelial lining of a vein and/or a valve may be grown from one or more tissue cultures, utilizing cloning of donor cell lines or other genetic engineering techniques (or "tissue engineering") known to those of skill in the art. Thus, as used herein, "a section of blood vessel" may include one or more of the following: a surgically resected segment of a blood vessel, with or without one or more valves; the endothelial lining of a blood vessel, taken from an in vitro or in vivo specimen; and one or more venous valves, taken from in vitro or in vivo specimens.

As noted above, the section of vein 10 or other blood vessel harvested preferably contains one or more valves 14, which occur naturally in the veins. The section of vein 10 may also not have a valve. The vein section 10 is sized so as to be the same length as the conduit 12. The vein section 10 is placed within the interior lumen of the conduit 12 and attached to the inside of the conduit 12 by suturing or other attachment methods. The natural vein graft 10 is biocompatible and therefore reduces problems associated with rejection of the conduit 12 and clotting around or in the conduit 12. In addition, the vein 10 provides a natural valve system 14 that is already used throughout the human body to prevent the backflow of blood. In the case of a xenograft, treatment of the graft with chemicals, such as glutaraldehyde, may be undertaken to remove living cells, including antigenic materials, from the connective tissue framework of the graft so as to reduce thrombogenicity and antigenicity.

Figure 3:
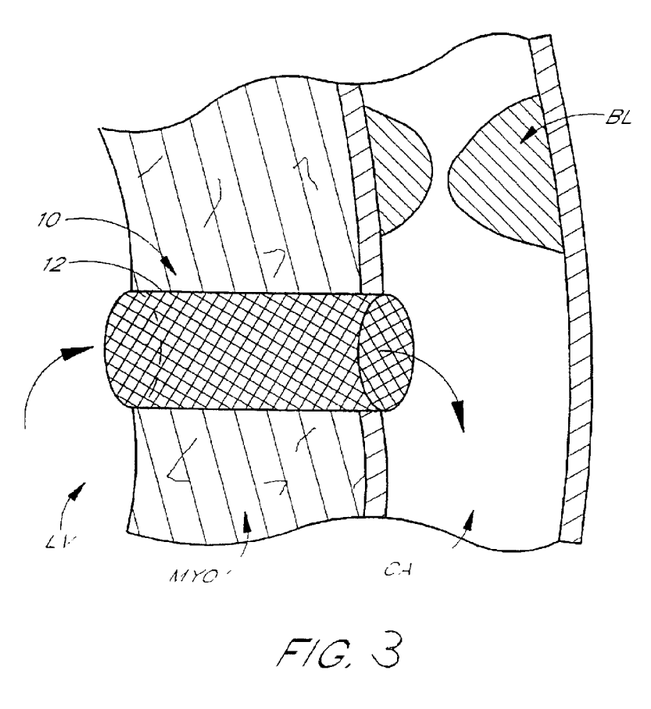
FIG. 3 is a close-up, cross-sectional view of a blockage or stenosis in the coronary artery, illustrating the conduit of the preferred arrangement positioned so as to bypass the blockage or stenosis.

Referring now to FIG. 3, a self-expanding conduit 12 having a section of vein 10 therein is introduced into the wall of the myocardium MYO as follows. A conduit delivery catheter (not shown), having the compressed conduit 12 mounted on its distal end, is advanced over a puncture mechanism and into the wall of the myocardium MYO at a site distal to the blockage or stenosis BL in the coronary artery CA. When the conduit 12 is properly seated in the myocardial wall MYO, its retaining sheath is withdrawn, allowing the conduit 12 to expand and open a passageway, or maintain patency of the passageway, from the left ventricle of the heart LV to the coronary artery CA. This allows oxygenated blood to flow directly from the left ventricle of the heart LV through the conduit 12 and to the coronary artery CA, bypassing the section of coronary artery CA that is blocked BL, as shown by the arrows in FIG. 3.

The conduit 12 may include attachment mechanisms not limited to hooks, barbs, large collars, and/or other methods to ensure that a seal is created between the coronary artery CA and the wall of the heart wall MYO, to prevent hemorrhaging and to prevent the threat of or actual conduit migration. When positioning and securing of the conduit 12 is completed, the remaining catheter assembly is removed, leaving the conduit 12 with the vein graft therein, in place in the body The present vascular conduit having a blood vessel graft incorporated therein provides significant improvements in the present treatment of blockages or stenoses in the coronary artery. Although the invention has been described in its preferred embodiments in connection with the particular figures, it is not intended that this description should be limited in any way by the foregoing.

What is claimed is:

1. A method of flowing blood from a heart chamber to a coronary vessel, the method comprising:
   providing a conduit with a first end and a second end;
   providing a natural valve;
   placing the conduit within a heart wall such that the first end of the conduit is open towards the heart chamber and the second end is open towards the blood vessel; and
   during diastole, restricting a flow of blood from the coronary vessel to the heart chamber via the natural valve.

2. The method of claim 1, wherein providing the natural valve includes providing a section of blood vessel containing at least one naturally occurring valve.

3. The method of claim 2, wherein the section of blood vessel is a human vein.

4. The method of claim 2, wherein the section of blood vessel is an autograft.

5. The method of claim 2, wherein the section of blood vessel is an allograft.

6. The method of claim 2, wherein the section of blood vessel is a xenograft.

7. The method of claim 1, wherein providing the natural valve includes providing the natural valve inside the conduit.

8. The method of claim 1, wherein the heart chamber is a left ventricle.

9. The method of claim 1, wherein the coronary vessel is a coronary artery.

10. A bypass system for implantation in a body of a patient, the system comprising:

a tube having a first end and a second end and being configured to be implanted in a heart wall such that the first end is open towards a heart chamber and the second end is open towards a coronary vessel, the tube being further configured to permit blood to flow therethrough from the heart chamber to the coronary vessel; and a natural valve configured to restrict blood flow from the coronary vessel to the heart chamber during diastole.

11. The system of claim 10, wherein the natural valve includes a section of blood vessel containing at least one naturally occurring valve.

12. The system of claim 11, wherein the section of blood vessel lines an interior of the tube.

13. The system of claim 11, wherein the section of blood vessel is a human vein.

14. The system of claim 11, wherein the section of blood vessel is an autograft.

15. The system of claim 11, wherein the section of blood vessel is an allograft.

16. The system of claim 11, wherein the section of blood vessel is a xenograft.

17. The system of claim 10, wherein the natural valve is disposed inside the tube.

18. The system of claim 10, wherein the heart chamber is a left ventricle.

19. The system of claim 10, wherein the coronary vessel is a coronary artery.

* * * * *